United States Patent [19]

McMahon et al.

[11] 4,394,074

[45] Jul. 19, 1983

[54] FIBEROPTIC-LIGHTED OPTICAL APPARATUS

[76] Inventors: William McMahon, 14102 Willow La., Westminster, Calif. 92683; Bernard Jensen, Rte. 1, Box 52, Escondido, Calif. 92025

[21] Appl. No.: 189,154

[22] Filed: Sep. 22, 1980

[51] Int. Cl.³ .............................................. A61B 3/10
[52] U.S. Cl. .................................. 351/206; 351/221; 354/62
[58] Field of Search ................ 351/6, 7, 16, 205, 206, 351/207, 208, 211, 221; 354/62; 350/96.18, 96.24

[56] References Cited

U.S. PATENT DOCUMENTS

| 4,102,563 | 7/1978 | Matsumura et al. | 351/7 |
| 4,219,258 | 8/1980 | Araki et al. | 351/7 |

FOREIGN PATENT DOCUMENTS

| 70397 | 4/1959 | France | 351/7 |

OTHER PUBLICATIONS

Whittaker Corporation Brochure for the Model 1984, Eye View Monitor and TV Pupillometer System, Oct. 1972.

*Primary Examiner*—R. A. Rosenberger
*Attorney, Agent, or Firm*—Francis X. LoJacono

[57] ABSTRACT

A fiberoptic-lighted optical apparatus for use in combination with a camera to photograph the convex surface of the iris of the eye for optimum depth of field and resolution, wherein the apparatus includes two separate fiberoptic light wands which are arranged to be positioned in close proximity to the eye and used to shape and accommodate the radius configuration of the eye, so that most of the light pattern therefrom is located in or adjacent to the pupil of the eye, each fiberoptic wand being selectively adjustable to be lighted by a quartz Halogen lamp, including a synchronized electronic flash tube which is placed in the focal point of the quartz Halogen light source, to provide a wide variety of lighting effects for selectively lighting either side of the eye for in-depth photography.

10 Claims, 11 Drawing Figures

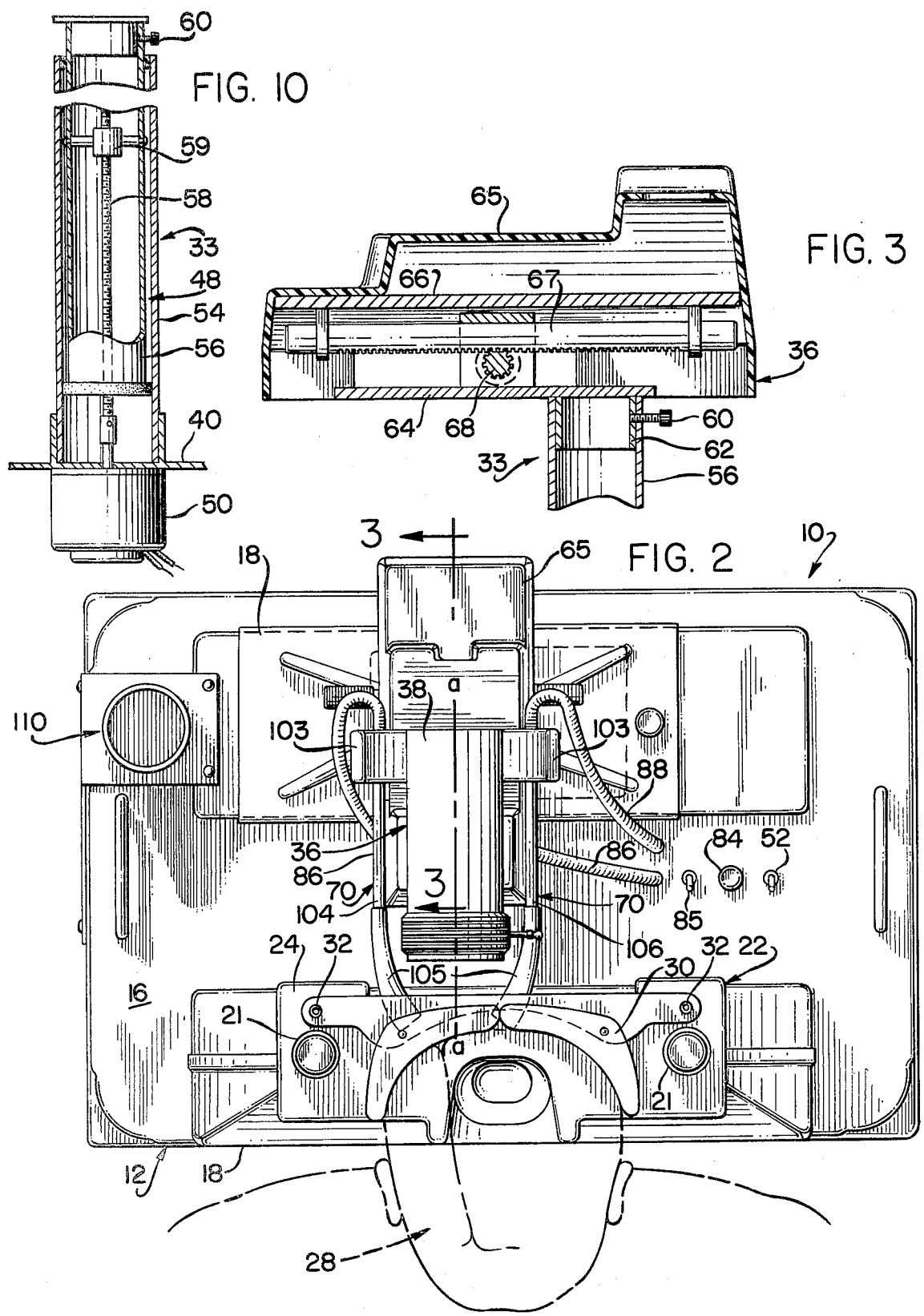

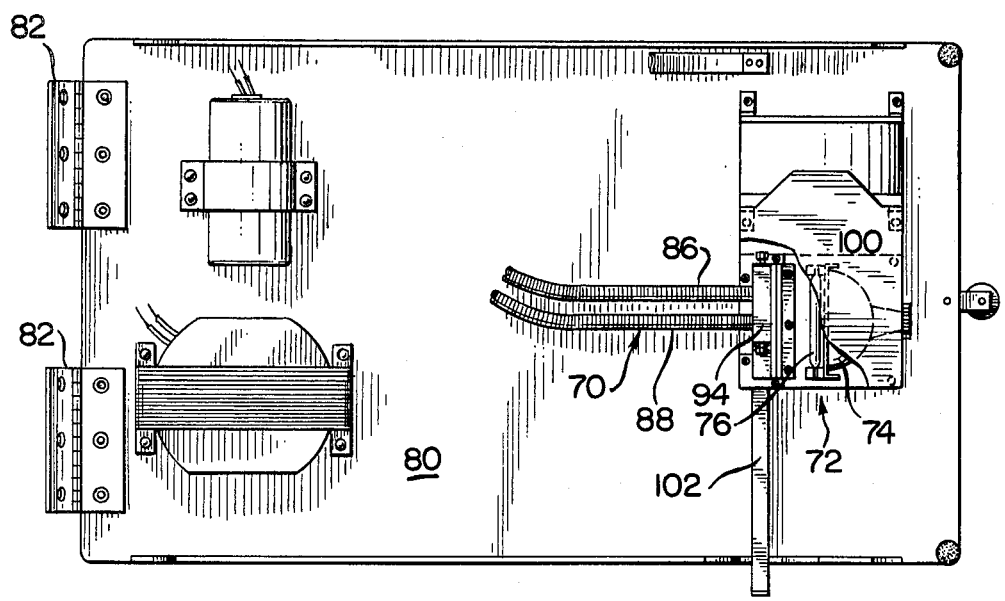
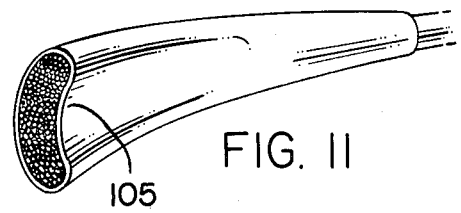
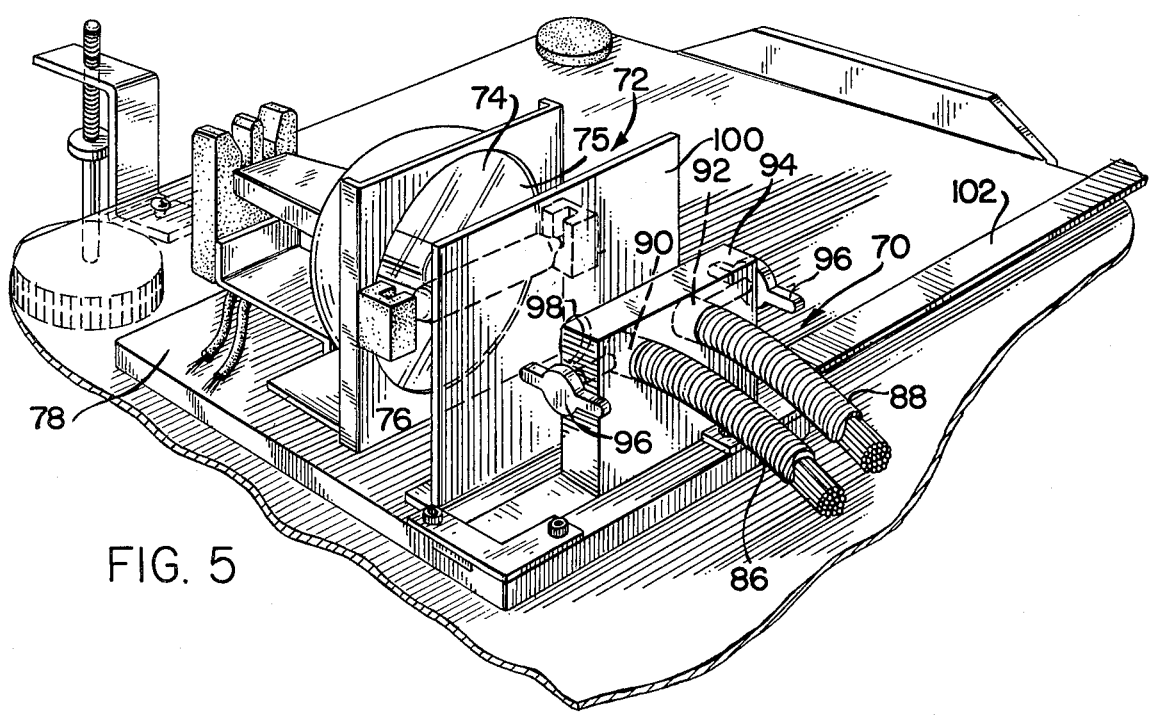

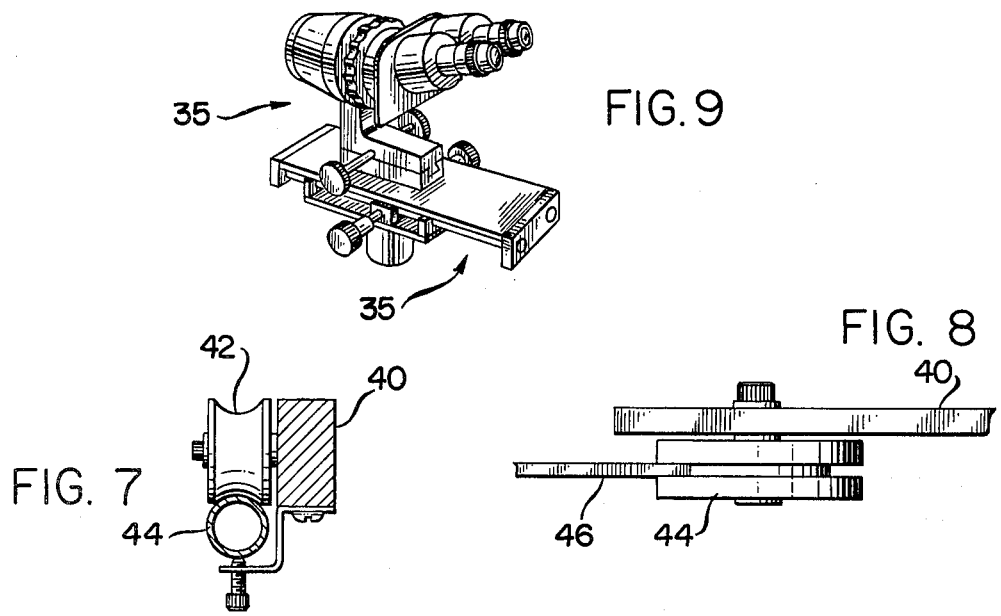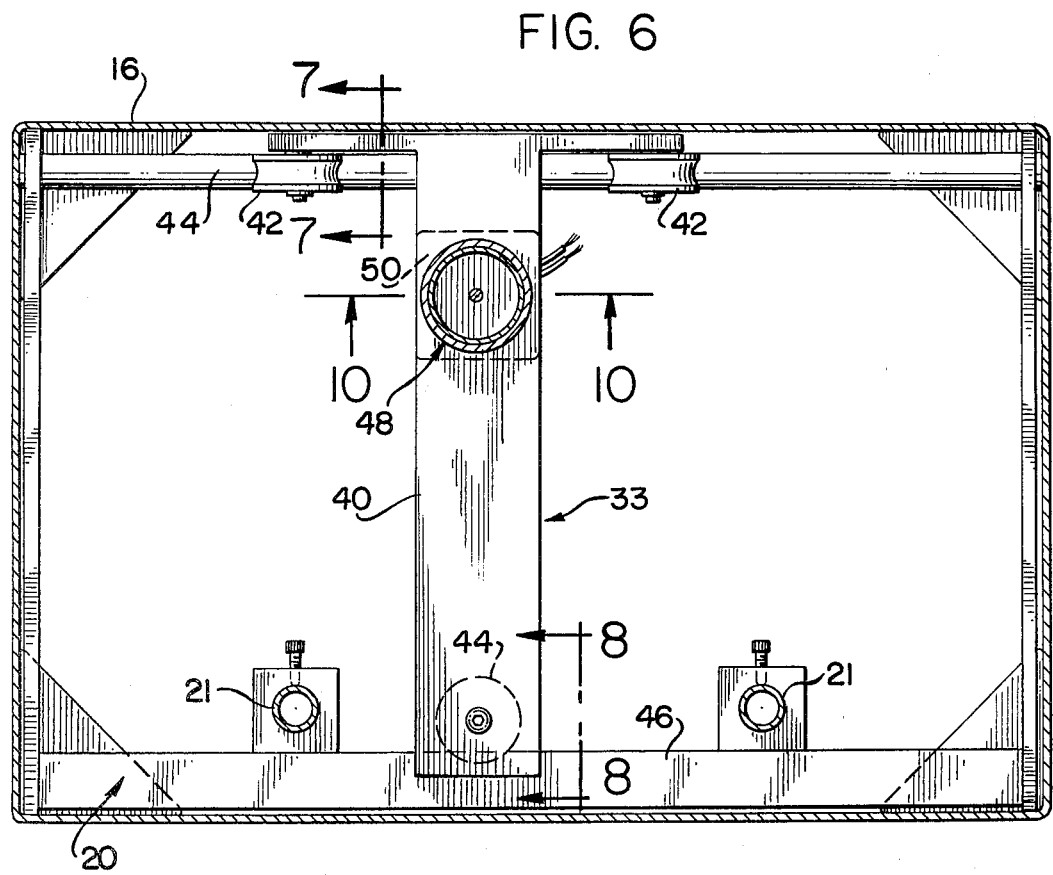

FIBEROPTIC-LIGHTED OPTICAL APPARATUS

BACKGROUND OF THE INVENTION

1. Field of the Invention

This invention relates to a fiberoptic-lighted optical apparatus, and more particularly to such an apparatus for microscopically examining and photographing the iris of the eye by means of the art of iridology.

2. Description of the Prior Art

It is well known in the art that various problems and difficulties are being encountered in providing suitable means for examining, studying and photographing the iris of the eye.

The iris of the eye, which resembles a movable curtain, is composed of an infinite number of very-fine small nerve filaments which receive impulses from every nerve center of the body. Thus, the iris becomes the visible outward terminus of the entire nervous system, enabling one to make the most exact analysis and/or diagnosis of the general condition of the body—i.e., the vascular and lymphatic systems, as well as the individual parts and organs.

Iridology is a unique science dealing primarily with the study of the anatomy of the front part of the eye and the interpretation of abnormal changes in pigment and structure. These changes act as reflex mechanisms having a direct relationship to various organs of the body. The term may be misleading, for the iris is only one part of the eye which the iridologist examines. Increased emphasis has been placed on the examination of the sclera, cornea, pupil, lens, etc. Thus, the term is generally used in most circles to incorporate the examination of other parts of the eye as well.

SUMMARY AND OBJECTS OF THE INVENTION

The present invention comprises a unique apparatus which allows one to make a complete and reliable analysis and/or diagnosis of the condition of the body through a controlled means of careful observation of the eye.

Accordingly, the present invention is provided with a suitable means comprising two fiberoptic wands, or bundles, which are arranged to transmit one or more effective lighting applications to the iris of the eye, without affecting the individual or the condition of the eye.

The fiberoptic wands consist of two separate wands of cool light, each having approximately 75,000–1.5 mil. optical-quality glass for light transmission. These light wands are placed at a very close proximity to the eye, and are used to shape and accommodate the radius configuration of the eye, so that most of the light pattern will be located adjacent to or in the iris.

The angle of the light approach to the iris using this type of fiber-lighting technique can be off-set at approximately thirty degrees to the right line of vision, which is the illuminating method that effects the least sensitivity to the eye. Therefore, greater depth and intensity of illumination may be utilized without discomfort to the individual.

These fiber bundles or wands are lighted by the use of a quartz Halogen lamp with a parabolic reflector and synchronized electronic flash tube which is positioned in the focal point of the same assembly, thus providing a wide variety of lighting techniques which—to our knowledge—were not heretofore considered in this type of application, or any other applications. This lighting technique is designed for lighting either side of the eye, alternately, for in-depth photography.

The apparatus further provides for the use of a stereoscoptic zoom microscope wherein a mounting carriage is arranged for mounting a camera or microscope on an adjustable tower for positioning the camera or microscope in an examining mode with the eye of an individual, when his head is supported in an oppositely disposed head-rest-support framework.

Thus, the present invention has for an important object to provide an apparatus of this type specifically for the scientist who employs the techniques of the art according to the theory and the study of iridology.

It is another object of the invention to provide a fiberoptic-lighted optical apparatus that includes two bundles of revolving and adjustable miniature pinpoints of light to create differences in shadow characteristics for true color radiations and balance, whereby natural-like color in the pictures will conform to the true coloring of the eye.

It is still another object of the invention to provide a fiberoptic-lighted optical apparatus that includes lighting effects by fiberoptics that carry cool light from the source to an angle at the eye that creates optimum contrast, and is in the least bothersome location for the subject.

Still a further object of the invention is to provide an apparatus of this character that includes in its light source a strobe light that is used for high-speed lighting, and to allow the pupil of the eye to expand so that fibers in the eye may be seen, even down to the deepest lesions thereof.

A still further object of the present invention is to provide an apparatus of this character wherein a camera used with this apparatus is capable of producing consistently high-quality pictures having the same size and contrast throughout.

It is still another object of the invention to provide an optical apparatus for taking pictures of the iris of the eye that is easy to adjust and is capable of incorporating interchangeable selective cameras or microscopes therewith.

It is a further object of the invention to provide an apparatus of this character that has relatively few operating parts.

It is still a further object of the invention to provide an apparatus of this character that is easy to service and maintain, and that includes features that establish a long-lasting span of use.

Still another object of the invention is to provide an apparatus for use in iridology that is relatively inexpensive to manufacture.

The characteristics and advantages of the invention are further sufficiently referred to in connection with the accompanying drawings, which represent one embodiment. After considering this example, skilled persons will understand that variations may be made without departing from the principles disclosed; and we contemplate the employment of any structures, arrangements or modes of operation that are properly within the scope of the appended claims.

BRIEF DESCRIPTION OF THE DRAWINGS

Referring more particularly to the accompanying drawings, which are for illustrative purposes only:

FIG. 2 is a top-plan view of the optical apparatus, illustrating the position of a subject's head with respect to the camera and the lighting system thereon;

FIG. 3 is an enlarged cross-sectional view taken substantially along line 3—3 of FIG. 2, showing the arrangement of the camera carriage;

FIG. 4 is a top-plan view of the mounting tray of the housing, showing the location of the light source with respect to the adjustable fiberoptic wands;

FIG. 5 is an enlarged perspective view of the light assembly;

FIG. 6 is an enlarged cross-sectional view taken substantially along line 6—6 of FIG. 1, to illustrate the positioning mechanism for the camera or microscope which allows for the adjustment thereof in a lateral and a vertical plan;

FIG. 7 is a cross-sectional view taken along line 7—7 of FIG. 6, showing the rail-support-member adjustable-chassis mounting;

FIG. 8 is an enlarged cross-sectional view of a portion of the chassis mounting taken substantially along line 8—8 of FIG. 6;

FIG. 9 is a pictorial view of a typical microscope unit adapted to be mounted to the present invention;

FIG. 10 is a cross-sectional view of the carriage-support tower for the camera or microscope; and FIG. 11 is a perspective view of one of the horned, crescent-shaped, light-emitting ends of the wands.

DESCRIPTION OF THE PREFERRED EMBODIMENT

Figure 1:
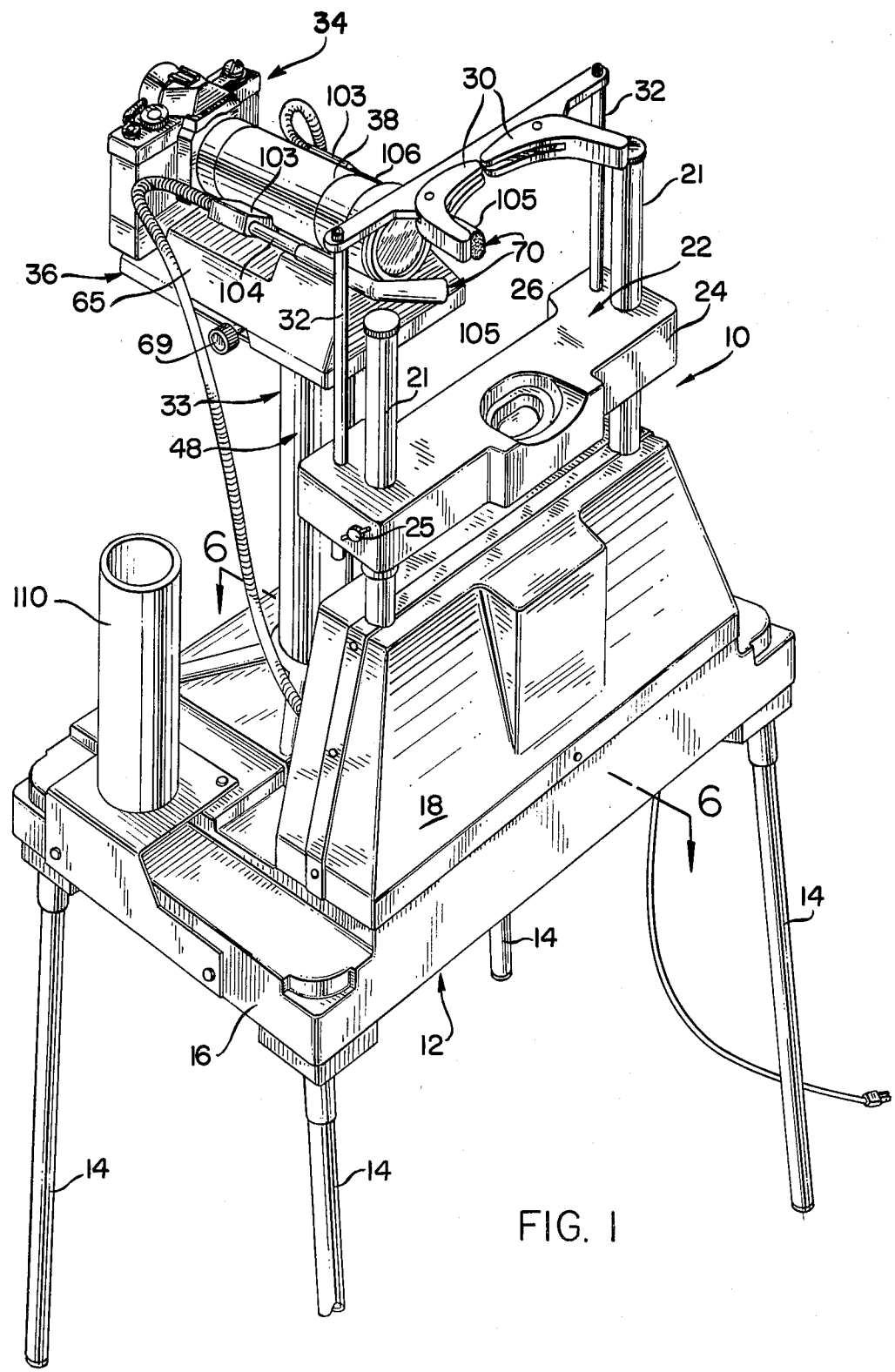
FIG. 1 is a pictorial view of the present invention having a camera positioned thereon.

Referring now to the drawings, and more particularly to FIG. 1 and FIG. 2, there is shown a fiberoptic-lighted optical apparatus, generally indicated at 10, which is designed primarily for use in the medical science of iridology—iridology being the study of the eye so that the knowledge obtained can aid in the diagnosis of the condition of the various organs and parts of the body. Thus, through the present invention the iris of the eye becomes the visible outward terminus of the condition of the nervous system, enabling one to analyze and/or diagnose the general condition of the body.

The fiberoptic-lighted optical apparatus comprises a main housing designated at 12, which is generally supported by a plurality of legs 14, wherein the housing includes removable covers 16 and 18. The housing further includes a frame structure, designated generally at 20, which is protected by cover 16, as seen in FIG. 6. Fixedly secured to frame structure 20 are a pair of vertically positioned posts 21, over which cover 18 is placed. These posts are adapted to adjustably receive a head-support means, indicated generally at 22. That is, the head-support means 22 comprises a head-support bridge member 24 adapted to be slidably positioned along the pair of post members 21—so as to be selectively located and locked into position by set screws 25. This arrangement allows for the subject's head to rest in the cradle 26 formed in bridge 24. The subject's head is indicated at 28 in FIG. 2. To aid in the proper alignment of one of the subject's eyes, head guides 30 are provided to engage the forehead thereof. Thus, the subject's chin is positioned in cradle 26, and the forehead is located and held in place by head-guide members 30, which can also be adjusted vertically on guide bars 32, if required. Once, the subject is comfortably positioned, the camera is then arranged properly with respect to the subject's eye to be photographed.

The present apparatus can be used for both taking pictures with a camera, indicated at 34; or it can be used in conjunction with a microscope, indicated at 35 in FIG. 9. However, since it is primarily used in photographing the iris of the eye, the following description will be related to such use.

Camera 34 may be any suitable make that is compatible with the overall operation of the apparatus, so that the camera can be mounted to an adjustable positioning means, indicated at 33. Removably mounted to the positioning means 33 is a camera carriage 36 which is, in itself, adjustable longitudinally with respect to the axis a—a of lens 38.

Accordingly, the positioning means 33 is adjustable both laterally and vertically with respect to the position of the subject's eye, whereby axis a—a of the lens is readily aligned with the iris of the eye. Axis a—a in FIG. 2 is illustrated as being aligned with the subject's left eye, which is being prepared for photographing. Positioning means 33 comprises a movable chassis 40 having a pair of wheels 42 mounted thereto, so as to be supported on a transverse rail 44, the rail being formed as part of the frame structure 20. Wheels 22 are located adjacent the rear of chassis 40; and a guide-roller member 44 is attached to the forward end thereof and arranged to engage a horizontal guide flange 46, as seen in FIGS. 6, 7 and 8. Thus, it can be understood that chassis 40 is movable laterally along rail 44 and guide flange 46.

In order to provide vertical alignment of camera 34 and lens 38, there is included an adjustable tower 48 which is remotely controlled by means of motor 50 mounted to the underside of chassis 40, and switch means 52 mounted to the housing cover 16. Tower 48 comprises a first stationary cylinder 54 having a coaxial movable cylinder 56 which slides up and down within the first cylinder 54 secured to chassis 40. This arrangement is illustrated in FIG. 10, wherein the inner movable cylinder 56 includes a drive means which is provided by motor 50 having a threaded shaft 58. Shaft 58 is received in a threaded journal 59 which is pivotally mounted within inner cylinder 56.

The upper free open end of inner cylinder 56 is provided with a set screw 60, whereby camera carriage 36 can be locked into position by means of collar 62 affixed to the camera carriage frame 64. Carriage 64 further comprises a housing body 65 having a configuration to accommodate the various known cameras. Body 65 is itself supported on a second carriage-frame member 66 which is adapted to be movable longitudinally by a rack 67 and a pinion 68. Rack 67 is secured to movable frame 66, and the mating pinion is rotatably supported in fixed frame 64. Pinion 68 includes a knob 69 located to one side of carriage 36, as seen in FIG. 1. This allows one to adjust the camera for focusing to the proper photographing position relative to the subject's eye.

Referring now to the unique dual-lighting system, there is comprised a light-transfer medium, generally indicated at 70, and a light-source means, generally designated at 72 and illustrated in FIG. 4 and FIG. 5. The lighting system is arranged to provide light directly and restrictively to the eye, and more particularly to the pupil and the iris of the eye which are the principle areas to be photographed for analysis and/or diagnosis.

The light-source means comprises two synchronized light elements—one being a quartz Halogen lamp 74 having a parabolic reflector 75 (tungsten Halogen, 150 watt, 21 volt, Sylvania, or equiv.) the other being an electronic flash strobe 76. Both light elements are mounted to a base plate 78 which is secured to the hinged bottom tray member 80, tray 80 being hingedly connected to frame structure 20 by hinges 82. It is important to note the positioning of each light element. That is, the flash strobe bulb 76 is positioned in front of and in close proximity to the Halogen lamp 74, so that the strobe is disposed at the focal point of the lamp—thus allowing the operator of the apparatus to light an area of the selected right or left eye by means of the Halogen lamp 74 alone. Hence, the camera can be adjusted for the proper position for focusing. If required, the quartz Halogen lamp 74 can be adjusted to emit varying degrees of light—from a very-low output to a very-high light factor—to provide sufficient light for photographing. This light-emitting condition is established by a variable light-control switch 84 locked on the cover 16 and adjacent the general on/off switches 85 and 52.

The light-transfer medium 70 is positioned between the lighting elements 74 and 75, and the subject's eye. The medium comprises first and second light bundles or wands 86 and 88—wand 86 being arranged to light the subject's left eye; while wand 88 is positioned to light the subject's right eye, as indicated in FIG. 2.

Each bundle or wand 86 and 88 comprises a multiplicity of individual light-transmitting strands. That is, each wand is made up of approximately 75,000–1.5 mil optical-quality-glass strands which transmit light in unison. The light-receiving ends 90 and 92 of the respective wands 86 and 88 are secured in a mounting block 94, and are locked into position by means of set screws 96. The ends are positioned adjacent each other so as to be selectively located in front of light passage 98 disposed in partition 100, which is interposed between the light source 72 and the light-receiving ends 90 and 92 of the respective wands.

Block 94 is provided with a means to adjust ends 90 and 92 so as to be selectively aligned with passage 98, whereby light will only be transmitted through one bundle at a time. Thus, in FIG. 5 wand 86 is positioned in front of passage 98, and in FIG. 4 wand 88 is located in front of the passage. The wand-adjusting means comprises a bar 102 slidably mounted to base plate 78 having block 94 affixed thereto for lateral movement with bar 102, which extends outwardly from one side of the housing framework or tray 80.

The light-emitting ends 104 and 106 of wands 86 and 88 are provided with means for controlling the pattern of light being emitted therefrom. That is, each end includes a horn-shaped member 105 which is formed having a crescent-shaped configuration, whereby a semi-circular light pattern is projected on or adjacent to the iris of the eye. FIG. 11 shows a crescent-shaped horn 105 arranged for light exposure to the left eye, horn 105 of end 106 being formed with an oppositely shaped crescent for the right eye. This arrangement provides a unique lighting technique that creates various shadow characteristics for true color radiation and balance in photographing the iris. The light-emitting ends 104 and 106 are oppositely disposed to each other. That is, each light-emitting end is disposed on opposite sides of lens 38, and are secured in place by a yoke member 103—yoke member 103 being attached to carriage 36, whereby ends 104 and 106 move with the carriage during focusing of the lens.

After the lens 38 and the camera 34 are in their proper arrangement for photographing, the camera is electronically connected in any known suitable manner with the light system, the connection thereof being similar to any known electronic flash unit. As camera 35 is activated and a picture is being taken, both lights 74 and 75 will be simultaneously energized. Thus, it can be seen that the subject is not aggravated by a constant light, so that the pupil of his eye is allowed to be in a normally apertured condition when the flash occurs.

However, as stated hereinbefore, various lighting effects are possible, whereby one may use the Halogen lamp by itself or together as described above, depending upon the particular requirements at the time of picture taking.

Further, when the camera 34 is replaced by the microscope 35, only the light from the Halogen lamp is required. Microscope 35 is provided with its own adjustable carriage 35a, and it operates similarly to carriage 36.

The apparatus is also provided with a support stand 110 which is adapted to receive and support microscope 35 and carriage 35a, or camera 34, when either is not being used.

The invention and its attendant advantages will be understood from the foregoing description; and it will be apparent that various changes may be made in the form, construction and arrangement of the parts of the invention without departing from the spirit and scope thereof or sacrificing its material advantages, the arrangement hereinbefore described being merely by way of example; and we do not wish to be restricted to the specific form shown or uses mentioned, except as defined in the accompanying claims.

We claim:

1. A fiberoptic-lighted optical apparatus for use with a camera for photographing the surface of the eye of a subject, wherein the apparatus comprises:
    a housing structure;
    means on said housing structure to support and position the subject's head with respect to said camera;
    means for mounting and adjusting said camera with respect to the eye of said subject;
    dual-light-source means adapted to be activated by the operation of said camera;
    a light-transfer medium adapted to receive light from said dual-light source, and project said light remotely therefrom to illuminate said eye of said subject;
    said dual-light-source means comprising:
    a first light source; and
    a second light source, wherein said second light source is positioned in front of and adjacent said first light source, whereby both of said light sources can be transmitted singularly or simultaneously through said light-transfer medium; and
    means for individually activating said first light source separately from said second light source, when said second light source is not required;
    said light-transfer medium comprising:
    a first bundle of light-transmitting fiberoptic strands; and
    a second bundle of light-transmitting fiberoptic strands, said strands being positioned adjacent each other, and in adjustable alignment with said first and second light sources, each bundle including a light-receiving end and a light-projecting end, said light-projecting end of each bundle being respectively positioned adjacent opposite sides of the lens of said camera;

means for selectively positioning said light-receiving end of said light-transmitting bundles in front of said dual-light-source means to selectively transmit light to one side or the other of said subject's eye.

2. An apparatus as recited in claim 1, wherein said second light source is interposed between said first light source and said light-receiving ends of said light-transmitting bundles, and positioned at the focal point therebetween.

3. An apparatus as recited in claim 2, wherein said means for selectively positioning said light-transmitting bundles comprises:

an adjustable mounting block adapted to selectively position said light-receiving ends of said bundles in alignment with said dual-light source; and a partition interposed between said dual-light source and said light-receiving ends of said bundles, said partition including a passage therein aligned with the focal point of said dual-light source, whereby said receiving end of said bundle can be selectively positioned in alignment with said passage, to allow the selected receiving end to be exposed to the light passing through said passage of said partition.

4. An apparatus as recited in claim 3, wherein each light-projecting end of said light-transmitting bundles includes a crescent-shaped horn, whereby light therefrom is projected on the pupil or iris of said eye to create various shadow characteristics.

5. An apparatus as recited in claim 4, wherein said first light source comprises a quartz Halogen lamp having a parabolic reflector, and wherein said second light source is a flash strobe.

6. An apparatus as recited in claim 5, wherein said means for mounting and adjusting said camera comprises:

a lineally movable chassis having a pair of wheels mounted thereon;

a rail affixed to said housing structure to receive said wheels thereon;

a guide roller mounted to said chassis;

a guide flange affixed to said housing structure in parallel arrangement with said rail, and adapted to receive said guide roller;

a support tower mounted to said chassis; and means for adjusting said tower vertically on said chassis.

7. An apparatus as recited in claim 6, wherein said means for supporting and adjusting the subject's head comprises:

a pair of support-post members affixed to said housing structure;

a head-support bridge adjustably secured to said support-post members; and a head guide mounted to said support bridge.

8. An apparatus as recited in claim 6, wherein said means for mounting and supporting said camera includes an adjustable carriage arranged to carry and position a microscope thereon.

9. An apparatus as recited in claim 6, wherein said means for mounting and supporting said camera includes:

an adjustable camera carriage adapted to be mounted in said support tower;

said carriage having means for adjusting said camera longitudinally thereof.

10. An apparatus as recited in claim 9, wherein said camera carriage includes means for securing said light-transmitting bundles, whereby said light-emitting ends are positioned on opposite sides of the camera lens, and are movable with said camera carriage.

* * * * *